US011230511B2

(12) United States Patent
Maury et al.

(10) Patent No.: US 11,230,511 B2
(45) Date of Patent: Jan. 25, 2022

(54) METHOD FOR THE ISOMERIZING DEHYDRATION OF A NON-LINEAR PRIMARY ALCOHOL FEEDSTOCK IN THE PRESENCE OF WATER INJECTION AND A CATALYST COMPRISING A FER OR MFS ZEOLITE

(71) Applicants: TOTAL RESEARCH & TECHNOLOGY FELUY, Seneffe (BE); IFP Energies Nouvelles, Rueil-Malmaison (FR)

(72) Inventors: Sylvie Maury, Saint Maurice d'Argoire (FR); Vincent Coupard, Villeurbanne (FR); Thibault Heinz, Solaize (FR); Guillaume Duplan, Saint Julien les Rosiers (FR); Joseph Lopez, Saint Julien les Rosiers (FR); Nikolai Nesterenko, Nivelles (BE)

(73) Assignees: TOTAL RESEARCH & TECHNOLOGY FELUY, Seneffe (BE); IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 16/347,858

(22) PCT Filed: Nov. 6, 2017

(86) PCT No.: PCT/EP2017/078307
§ 371 (c)(1),
(2) Date: May 7, 2019

(87) PCT Pub. No.: WO2018/087033
PCT Pub. Date: May 17, 2018

(65) Prior Publication Data
US 2019/0270687 A1 Sep. 5, 2019

(30) Foreign Application Priority Data
Nov. 8, 2016 (FR) ...................................... 1660803

(51) Int. Cl.
*C07C 1/22* (2006.01)
*C07C 5/27* (2006.01)
(Continued)

(52) U.S. Cl.
CPC ............. *C07C 5/2775* (2013.01); *B01J 29/65* (2013.01); *C07C 1/24* (2013.01); *C07C 11/09* (2013.01);
(Continued)

(58) Field of Classification Search
None
See application file for complete search history.

(56) References Cited

U.S. PATENT DOCUMENTS 9,233,886 B2    1/2016  Adam et al.
10,099,969 B2   10/2018 Vivien et al.
(Continued)

FOREIGN PATENT DOCUMENTS

WO    2011/113834 A1    9/2011
WO    2016/046242 A1    3/2016

OTHER PUBLICATIONS

International Search Report dated Jan. 4, 2018 issued in corresponding PCT/EP2017/078307 application (3 pages).
(Continued)

*Primary Examiner* — Philip Y Louie
(74) *Attorney, Agent, or Firm* — Millen, White, Zelano & Branigan, PC; Ryan Pool

(57) ABSTRACT

A process for the isomerizing dehydration of a feedstock including a primary monoalcohol, alone or as a mixture, of formula R—CH$_2$—OH, wherein R is a nonlinear alkyl radical of general formula $C_nH_{2n+1}$ where n is an integer between 3 and 20, the process taking place
in the gas phase at a weighted average temperature between 275° C. and 400° C., at a pressure between 0.3
(Continued)

MPa and 1 MPa and at a WWH (weight per weight per hour) between 5 and 10 $h^{-1}$, in the presence of a catalyst containing at least one silicic binder and at least one zeolite having at least one series of channels, the opening of which is defined by a ring of 8 oxygen atoms (8MR), process wherein vaporized feedstock entering the reactor has a weight content of water of from 4% to 35%.

17 Claims, 2 Drawing Sheets

(51) Int. Cl.
    *B01J 29/65*     (2006.01)
    *C07C 1/24*     (2006.01)
    *C07C 11/09*     (2006.01)

(52) U.S. Cl.
    CPC ...... *C07C 2521/08* (2013.01); *C07C 2529/65* (2013.01)

(56) References Cited

U.S. PATENT DOCUMENTS

| | | |
|---|---|---|
| 2013/0204057 A1 | 8/2013 | Adam et al. |
| 2017/0341996 A1 | 11/2017 | Vivien et al. |

OTHER PUBLICATIONS

J. Taylor et al., "Dehydration of Fermented Isobutanol for the Production of Renewable Chemicals and Fuels", Topics in Catalysis, vol. 53 No. 15-18 (2010) pp. 1224-1230.

METHOD FOR THE ISOMERIZING DEHYDRATION OF A NON-LINEAR PRIMARY ALCOHOL FEEDSTOCK IN THE PRESENCE OF WATER INJECTION AND A CATALYST COMPRISING A FER OR MFS ZEOLITE

TECHNICAL FIELD OF THE INVENTION

The present invention relates to an improved process for producing alkenes from a feedstock comprising a primary monoalcohol, alone or as a mixture, of formula R—CH$_2$—OH, wherein R is a nonlinear alkyl radical of general formula $C_nH_{2n+1}$ where n is an integer between 3 and 20 (such as isobutanol), the process taking place in the presence of an optimal amount of water injected with the feedstock. The process has a high performance, in particular in terms of stability of the conversion and/or selectivity for desired products. This feedstock may be obtained by chemical processes or by fermentation processes. This process uses a shaped catalyst based on a zeolite comprising at least one series of channels, the opening of which is defined by a ring of 8 oxygen atoms (8MR).

The alkenes obtained have a significant advantage in the field of the petrochemical industry and of organic synthesis. This is the case in particular for isobutene, but-1-ene and but-2-ene.

PRIOR ART

Isobutene is a key molecule in petrochemistry and for the synthesis of gasoline additives such as ETBE and MTBE. The vast majority of publications relate to the production of isobutene from linear butanols, these being more easily produced by conventional (ABE) fermentation pathways than isobutanol. Recent developments have however made it possible to greatly improve the fermentation yields of isobutanol, making this feedstock accessible and available at an attractive cost.

Document WO 2009/074798 describes a process for converting n-butanol into di-isobutene (2,4,4-trimethylpentene), which process includes a step of dehydration with isomerization of the n-butanol. During this step, at least 20 wt % of isobutene is obtained in the effluent and the example shows that around 31% of isobutene are produced.

The process recommends the addition of water to the feedstock in the water:n-butanol volume ratio of 1 to 70, or else 5-50 or 10-35, which would have the effect of improving the isobutene productivity and the isobutene selectivity.

However the comparative example with a ZSM-23 zeolite shows that the addition of water does not provide any improvement in the isobutene selectivity relative to the total butenes. This presence of water has, on the other hand, the advantage of not lowering the selectivity, and therefore makes it possible to not dry the feedstock, which is economically favorable as the patent indicates.

The other zeolite tested is Theta-1 which displays an n-butenes selectivity of 53% relative to the total butenes.

The catalyst comprises a unidirectional zeolite without other interconnected channels. The zeolites exemplified are Theta-1 (of TON type with 10MR channel opening) and ZSM-23 (of MTT type with 10MR channel opening). The SAPO-11 zeolite (also with 10MR) is cited. Ferrierite is also cited, without being exemplified, but on the one hand it does not correspond to the teaching of this document since it has 2 series of interconnected channels (8MR and 10MR) and on the other hand no means for adjusting the degree of isomerism is described.

Document WO 2011/113834 describes the simultaneous dehydration and skeletal isomerization of isobutanol in the presence of crystalline silicate catalysts comprising at least 10MR channels, which are optionally dealuminated and optionally phosphorus-modified, of the FER (8 and 10MR channels), MWW (10 and 10MR), EUO (10MR), MFS (8 and 10MR), ZSM-48 (10MR), MTT (10MR), MFI (10 and 10MR), MEL (10MR) or TON (10MR) group having an Si/Al ratio greater than 10, silicoaluminophosphate molecular sieves of the AEL (10MR) group, or silica-, zirconia-, titania- or fluoro-alumina on zeolite catalysts.

The process takes place with a WHSV with respect to the alcohol of at least 1 h$^{-1}$ and a temperature of from 200° C. to 600° C. The example is carried out by passing an isobutanol feedstock/water (weight ratio 95:5) over a powdered FER zeolite with Si/Al=33 at 375° C., 2 bar and at high WHSV (12.6 h$^{-1}$). Under these conditions, the maximum proportion achieved of n-butenes in the butenes (isobutene plus linear butenes) is 58.4%, a value higher than the one expected during the isomerization of isobutene at the thermodynamic equilibrium of the butenes.

The dehydration of C$_4$ alcohols over acid solids is generally accompanied by the positional isomerization of the alkene formed. These two reactions are actually concomitant, since the positional isomerization of the double bond of the alkene is as fast as the dehydration reaction of the C$_4$ monoalcohol. In the case of isobutanol, the isobutene formed is easily protonated (formation of a tertiary carbocation) and may then undergo secondary reactions leading to a degradation of the selectivity for the desired product and also to a deactivation of the catalyst by coking.

Chadwick et al. (Chadwick et al., Chem. Commun., 2010, 46, 4088-4090) test Theta-1, ZSM-23, ferrierite (Si/Al=20) and ZSM-5 (10MR) zeolites in dehydration/isomerization at 400° C. to carry out the simultaneous dehydration and isomerization of n-butanol to obtain isobutene. They demonstrate a loss of isomerizing activity of the ferrierite for the formation of isobutene over time and attribute it to a negative effect of the water formed by the dehydration reaction. This is not observed with the other zeolites and ferrierite is the zeolite which displays the most degraded stability.

OBJECTIVE AND ADVANTAGE OF THE INVENTION

The invention relates to a process for the isomerizing dehydration of a feedstock comprising a primary monoalcohol, alone or as a mixture, of formula R—CH$_2$—OH, wherein R is a nonlinear alkyl radical of general formula $C_nH_{2n+1}$ where n is an integer between 3 and 20, said process taking place in the gas phase at a weighted average temperature between 275° C. and 400° C., preferably 300-400° C., at a pressure between 0.3 MPa and 1 MPa, preferably 0.5 MPa and 1 MPa, and at a WWH (weight per weight per hour) between 5 and 10 h$^{-1}$, preferably 7-10 h$^{-1}$, in the presence of a catalyst comprising at least one silicic binder and at least one zeolite having at least one series of channels, the opening of which is defined by a ring of 8 oxygen atoms (8MR), process wherein vaporized feedstock entering the reactor has a water weight content from 4% to 35%, preferably from 4% to 15%, and very preferably of 6-15%.

The process according to the invention makes it possible to rapidly produce a mixture of alkenes rich in linear alkenes. Specifically, through the choice of the amount of water present in the feedstock entering the reactor and of the zeolite catalyst, a very high conversion (of more than 98%) of the alcohol is obtained. The linear alkenes selectivity is improved compared to a process without water and the total alkenes selectivity is greater than 97%. Another advantage is that the stabilization time of the butenes yield is almost immediate. The thermal stability of the alcohol is itself also largely improved in the presence of an optimized proportion of water provided by the feedstock. The selectivity for undesired byproducts (such as isobutyraldehyde) is limited in particular at high temperature (at 300-400° C., or even better at 350-400° C.).

These beneficial effects result from the protective action of the water towards said monoalcohol. It probably prevents the thermal degradation of the alcohol and probably makes it possible to reduce the non-selective coke formation, which protects the catalyst from significant degradation by maintaining its selectivity.

This addition also makes it possible to limit the formation of undesired byproducts (such as aldehydes), which products could be formed in the absence of catalyst on the metal walls, for example in the lines conveying the feedstock to the reactor.

DETAILED DESCRIPTION OF THE INVENTION

Feedstock

In accordance with the invention, the feedstock to be treated in the process according to the invention comprises at least one alcohol of formula R—CH$_2$—OH, R being a nonlinear alkyl group of general formula C$_n$H$_{2n+1}$ where n is an integer between 3 and 20. In one particular embodiment, n is an integer between 3 and 10.

The primary alcohol is preferentially selected from isobutanol or 2-methyl-1-butanol, alone or as a mixture. Very preferentially, the primary alcohol is essentially isobutanol. Preferably, the feedstock comprises isobutanol as the only alcohol.

The feedstock may originate from chemical or biochemical processes, for example fermentation processes. In particular, this feedstock may be derived from lignocellulosic biomass fermentation processes.

Said feedstock may also comprise organic impurities (such as methanol, ethanol, n-butanol, aldehydes, ketones, and the corresponding carboxylic acids, for example furanic acid, acetic acid, isobutyric acid).

Water is optionally added to the feedstock to be treated, so that the vaporized feedstock entering the reactor has a weight content of water of 4-35%, preferably of 4-15%, and very preferably of 6-15%. Very preferably, the weight content of water is 4-10% and 6-10%.

Generally, the water is added to the feedstock to be treated upstream of the reactor, the feedstock to be treated being at a temperature below 300° C., or even below 275° C. It is added to the vaporized feedstock to be treated, or the mixture is vaporized.

The feedstock entering the reactor is in gaseous form. It comprises, and preferably consists of, said monoalcohol, impurities and water.

The feedstock entering the reactor comprises at least 40% and generally from 55% to 96% by weight of said alcohol. Said impurities represent at most 10 wt % of the feedstock entering the reactor, or even at most 5%.

Owing to this presence of water in a targeted amount, the pre-coking of the catalyst, and in particular of the ferrierite-based catalyst, proved unnecessary; the process according to the invention therefore takes place without pre-coking. Pre-coking is an operation that aims to selectivate the catalyst by a deposition of organic coke originating either from an exposure of the catalyst to the customary feedstock, often under conditions harsher than the operating conditions chosen for the dehydration reaction of the alcohol, or by the use of a particular feedstock. The operation was, before the invention, a prerequisite for the customary operation of the unit.

Process

The process (reactor) is operated in the gas phase, at a weighted average temperature between 275° C. and 400° C., preferably 300-400° C., at a pressure between 0.3 MPa and 1 MPa, preferably 0.5 MPa and 1 MPa, or else 0.3-0.9 MPa or else 0.5-0.9 MPa, at a WWH between 5 and 10 h$^{-1}$, preferably 7-10 h$^{-1}$.

WWH is understood to mean "weight per weight per hour", i.e. the mass flow of primary alcohol in the feedstock at the reactor inlet divided by the mass of catalyst in said reactor. This concept is also sometimes denoted under the acronym WHSV or "weight hourly space velocity".

The weighted average temperature (denoted by WAT) is understood to mean the average temperature in the catalyst bed, the bed being all of the beds present in the reactor, in which beds the catalytic reaction takes place, calculated along the axis of the flow through said bed. Namely a bed of length L and of surface area S, the reactive mixture flowing along the longitudinal axis x of this bed, the inlet into the catalyst bed forming the origin of the axis (x=0), the weighted average temperature, denoted by WAT, is expressed according to the following formula:

$$WAT = \frac{1}{L}\int_0^L T(x)dx$$

Since the reaction is endothermic and the reactor operates either in isothermal mode, or in adiabatic mode, the weighted average temperature will be representative of the reaction temperature.

The reaction takes place in one or more reactors and each reactor is operated under identical conditions. The WAT of each of the reactors is adjusted to a value between 275° C. and 400° C. Thus, in the remainder of the description, the term "the reactor" denotes both the reactor of this step when this step comprises only one reactor, and each of the reactors of this step, when this step comprises more than one reactor.

Said catalyst is positioned in one or more fixed beds, which may be operated in upflow, downflow or radial flow.

Since the dehydration reaction is endothermic, the heat input is achieved by any heating means known to a person skilled in the art.

Before coming into contact with the feedstock to be treated, the catalyst is activated by any means known to a person skilled in the art, for example by heat treatment in air.

Catalyst

In accordance with the invention, the catalyst used comprises a zeolite having at least one series of channels, the opening of which is defined by a ring of 8 oxygen atoms (8MR) as defined in the classification "Atlas of Zeolite Structure Types, Ch. Baerlocher, L. B. Mc Cusker, D. H. Olson, 6th Edition, Elsevier, 2007, Elsevier, p 142". This zeolite is shaped with a binder.

According to one particular embodiment, the zeolite may also advantageously contain at least one series of channels, the pore opening of which is defined by a ring containing 10 oxygen atoms (10 MR), such as FER or MFS.

Said zeolite is advantageously selected from zeolites having 8 and 10MR channels such as zeolites of FER and MFS structural type, taken alone or as a mixture. The zeolite is more advantageously selected, in the FER type, from ferrierite, FU-9, ISI-6, NU-23, ZSM-35 zeolites, and for the MFS type it is the ZSM-57 zeolite, taken alone or as a mixture. Said zeolite is very advantageously of FER type and preferably is ferrierite. Preferably, said zeolite consists of ferrierite. Preferably, it has not undergone a treatment for introducing alkali metal elements, alkaline-earth metal elements or other elements. It may nevertheless have been dealuminated. It is in H (hydrogen) or $NH_4$ (ammonium) form.

Preferably, the ferrierite has an Si/Al molar ratio of 8 to 70, preferably selected between 10 and 50.

The content of zeolite in the catalyst is between 50% and 90% by weight, preferably between 60% and 80% by weight.

The catalyst also comprises a silicic binder, generally the binder is based on silica, in particular amorphous silica.

Preferably, the silicic binder consists of silica (apart from the impurities, these having no catalytic effect).

The content of binder in the catalyst is between 10% and 50% by weight, preferably between 20% and 40%.

Very advantageously, the catalyst consists of at least one zeolite having at least one series of channels, the opening of which has 8 oxygen atoms (8MR) and a silicic binder. Preferably, said catalyst consists of ferrierite zeolite and of silicic binder. Preferably, said catalyst consists of ferrierite zeolite and of silica, and in particular of amorphous silica. The catalyst may optionally contain impurities in a small amount having no technical effect on the conversion/selectivity of the catalyst.

The catalyst is shaped, preferably in the form of cylindrical or multilobed extrudates, beads or any other method known to a person skilled in the art with the exception of powder. Specifically, the binder is needed to obtain a hierarchical porosity which enables most of the zeolite crystals to be supplied with reactant without undergoing a significant pressure drop per meter of catalyst bed. Furthermore, the binder has the role of spacing out the active sites so as to reduce the occurrence of a biomolecular reaction, a reaction that gives in this case undesired products.

Moreover, the binder is generally useful for giving a mechanical strength to the catalyst and enabling, throughout the catalytic cycle thereof, loading/unloading operations and transport of the catalysts without loss of material in the form of fines.

Catalyst Preparation Process

Said catalyst used in the process according to the invention is advantageously prepared according to a preparation process comprising at least the following steps:
1) a step of mixing at least one zeolite powder, preferably in proton or ammonium form, with at least one silicic binder, for example an amorphous silica powder
2) a step of adding a solvent, advantageously water, and optionally peptizing agent; preferably a peptizing agent is used
3) a step of shaping the paste mixture obtained at the end of step 2), for example by extrusion
4) a step of heat treatment of the shaped material obtained at the end of step 3) at 50-800° C. in air.

The silicic binder used in step 1 is well known to a person skilled in the art, it is selected for its inert nature with respect to the operating conditions and in particular with respect to the presence of water in the process.

A source of silicic binder may be a precipitated silica or a silica derived from by-products such as fly ash, for example aluminosilicate or calcium silicate particles, and silica fume. Use could advantageously be made of a colloidal silica, that is for example in the form of a stabilized suspension, for instance the commercial products such as Ludox® or Klebosol®. An amorphous silica powder may advantageously be used in step 1).

The zeolite powder and the silicic binder (preferably in powder form) are advantageously mixed in the presence of a solvent (step 2), preferably water in which a peptizing agent may advantageously be dissolved in order to obtain a better dispersion of the binder. The consistency of the paste is adjusted by means of the amount of solvent.

The peptizing agent used during this step may advantageously be an organic or inorganic acid or base such as acetic acid, hydrochloric acid, sulfuric acid, formic acid, citric acid and nitric acid, alone or as a mixture, aqueous ammonia, an amine, a quaternary ammonium compound, selected from alkyl ethanolamines or ethoxylated alkylamines, tetraethylammonium hydroxide and tetramethylammonium.

The peptizing agent may advantageously be selected from mineral bases such as sodium hydroxide or potassium hydroxide.

During the shaping step 3, the mixed paste is extruded through a die, the geometry of which will impose the shape of the catalyst.

EXAMPLES

The dehydration step is carried out in a catalytic test unit containing 1 reactor (Ex 1) or 2 reactors (Ex 2-4) each comprising a fixed bed operating in downflow mode. The catalyst is loaded, in the form of extrudates having a length of 2 to 4 mm, into each 316L stainless steel reactor having an internal diameter of 13 mm. The catalyst is then activated at 450° C. under 6 l/h of air over a hold time of one hour, after a temperature rise of 10° C./min, the temperature is then lowered to the test temperature under 6 l/h of nitrogen in order to eliminate the air present in the system before injection of the alcohol feedstock.

Water is added to the dry isobutanol feedstock. The feedstock is an isobutanol/water mixture in a variable weight ratio. It is vaporized in lines heated at 150-180° C. upstream of the first reactor then injected into the catalytic reactor. The pressure is maintained at 8 bar.

The analysis of the total effluent is carried out at the outlet of the reactor on a gas chromatograph in a line equipped with two columns, which makes it possible to determine the conversion of the isobutanol, the selectivities for various products and in particular the butenes selectivity and the fraction of linear butenes in the butene cut, which fraction it is sought to maximize. The analyzer also makes it possible to measure the selectivity for by-products such as products containing 5 carbon atoms or more (referred to as C5+), alkanes, carboxylic acids or ethers. The measurement of the average conversion achieved during the 24 h of the return point after 72 h of test is compared to the average conversion during the first 24 hours at WWH of 7 $h^{-1}$ and makes it possible to evaluate the loss of activity during the test.

WWH corresponds to the hourly weight of feedstock injected relative to the weight of catalyst.

The figures relate to the examples.

Example 1 (in Accordance with the Invention)

The catalyst A is prepared by mixing 70% of commercial ferrierite powder in ammonium form having an Si/Al atomic ratio of 20 and 30% of a commercial silica source, and 9% of a commercial silica source (the weight fractions are calculated relative to the total dry weight of the powders) by mixing with an aqueous solution of triethylammonium TEAOH, extrusion, drying then calcination.

The catalyst A is used in the catalytic test as described above, the feedstock flow rate is 10.5 g/h, which corresponds to a WWH of 7 h$^{-1}$ for a mass of 1.5 g of catalyst loaded.

The test is conducted with a feedstock containing 30 wt % $H_2O$.

A complete conversion of the isobutanol and a stable performance can be observed (FIG. 1).

The ratio of isobutenes to all butenes is also stable (+4% in 160 h).

Example 3

The test is conducted with a 100 wt % isobutanol feedstock. The very rapid deactivation and an increase in the ratio of isobutenes to all butenes of 30% in 120 h can be observed.

| Water in the feedstock (wt %) | T (° C.) | Conversion (%) | Initial n-butenes/ total butenes (%) | n-butenes/ total butenes after 72 h (%) | Initial C4= selectivity (%) | C4= selectivity after 72 h (%) | Initial isobutyraldehyde selectivity (%) | Isobutyraldehyde selectivity after 72 h (%) |
|---|---|---|---|---|---|---|---|---|
| Not in accordance with the invention ||||||||||
| 0 | 300 | 99.1 | 82.4 | 84.1 | 89.9 | 97.8 | 0.06 | 0.06 |
| 0 | 400 | 99.8 | 65 | 77.0 | 88.9 | 98.7 | 0.11 | 0.41 |
| In accordance with the invention ||||||||||
| 7 | 300 | 98.5 | 82.6 | 84.1 | 94.4 | 97.8 | 0.06 | 0.06 |
| 7 | 400 | 98.9 | 69.8 | 77.0 | 94.3 | 98.8 | 0.06 | 0.07 |

The stabilization time of the selectivity for desired products (total butenes and linear butenes) is much faster in the presence of 7 wt % water in the feedstock than in the presence of an undiluted feedstock. Specifically, the initial butenes selectivity is greater than 94% in the presence of water whereas it is less than 90% in the absence of water in the feedstock. Equivalent butenes selectivity levels are achieved only after 72 h under feedstock.

This emphasizes the effect of the water added to the feedstock on the selectivation of the catalyst. The selectivity for linear butenes, which is the targeted product, is thus considerably greater in the presence of water in the feedstock.

The process achieves yields of butenes and in particular of linear butenes that are much higher starting from injection of the feedstock and thus the yield of the process is greatly improved.

Furthermore, the selectivity for undesired byproducts (isobutyraldehyde) is limited at high temperature in the presence of water in the feedstock.

Examples 2-3: Tests Under Isothermal Conditions

Example 2 with 30% Water (in Accordance with the Invention)

The catalyst A is used in a catalytic test under isothermal conditions.

For the test, 200 ml of catalyst are loaded in the form of extrudates into two reactors (100 ml of catalyst per reactor). The feedstock flow rate is 770 g/h, which corresponds to a WWH of 7.0 h$^{-1}$.

The feedstock is preheated before entry into the first reactor Rx1 in order to have a weighted average temperature of the catalyst bed of 350° C. Between the two reactors, the feedstock is also preheated to ensure a weighted average bed temperature of 350° C. in the second reactor.

Example 4: Test Under Isothermal Conditions with 10% Water (in Accordance with the Invention)

Fresh catalyst A is used in the catalytic test under isothermal conditions. For the test, 200 ml of catalyst in the form of extrudates are loaded into two reactors (100 ml of catalyst per reactor). The feedstock flow rate is 770 g/h, which corresponds to a WWH of 7.0 h$^{-1}$. The feedstock is preheated before entry into the reactor Rx1 in order to have a weighted average temperature of the catalyst bed of 315° C. Between the two reactors, the feedstock is also preheated to ensure a weighted average temperature of the catalyst bed of 315° C. in the second reactor.

The test is carried out with a feedstock containing 10 wt % water. The catalyst demonstrated a stable performance over more than 2000 hours (FIG. 2).

Figure 1:
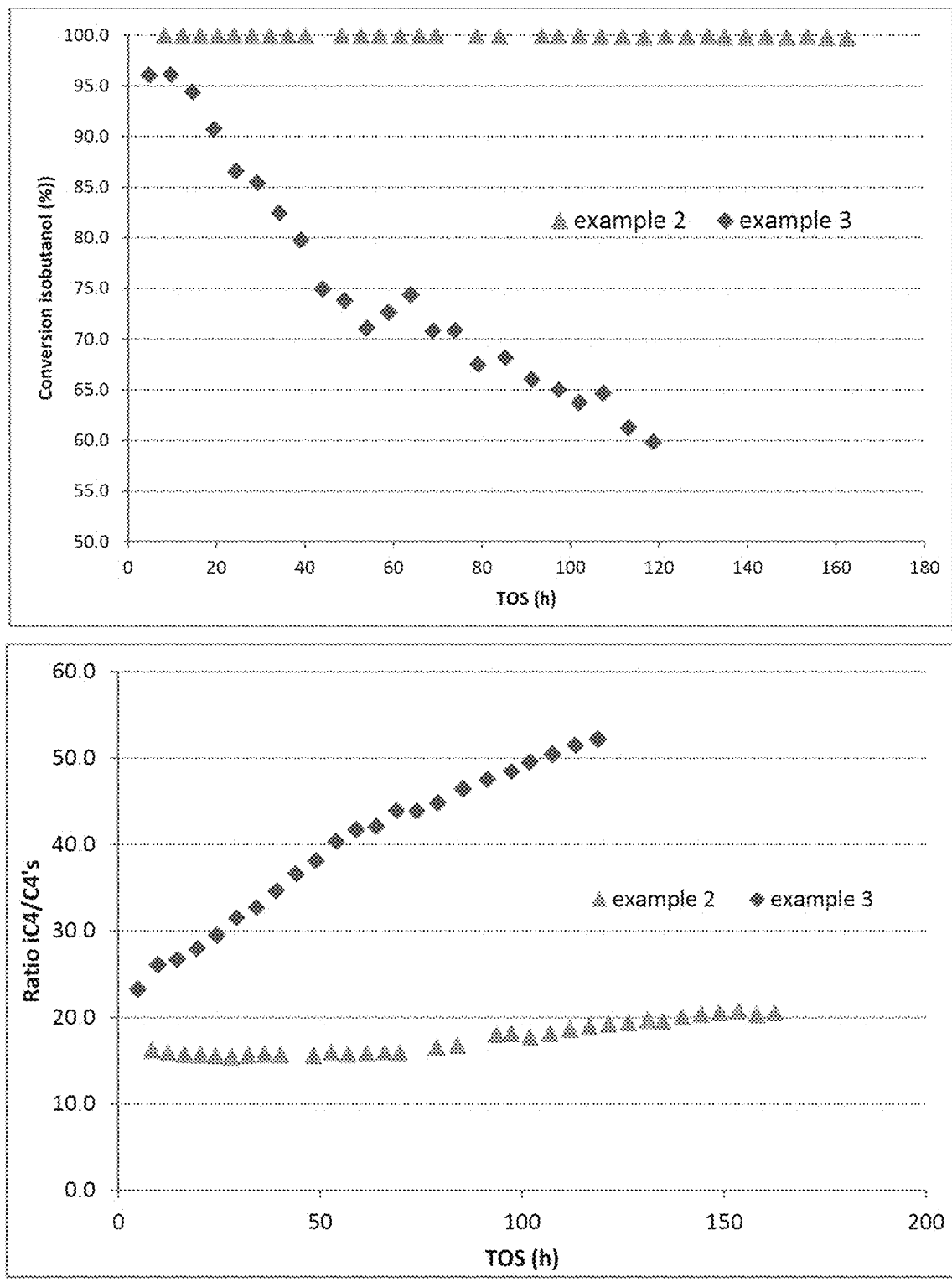
FIG. 1 illustrates for example 2 that a complete conversion of the isobutanol and a stable performance can be observed, and that the ratio of isobutenes to all butenes is also stable (+4% in 160 h).
Figure 2:
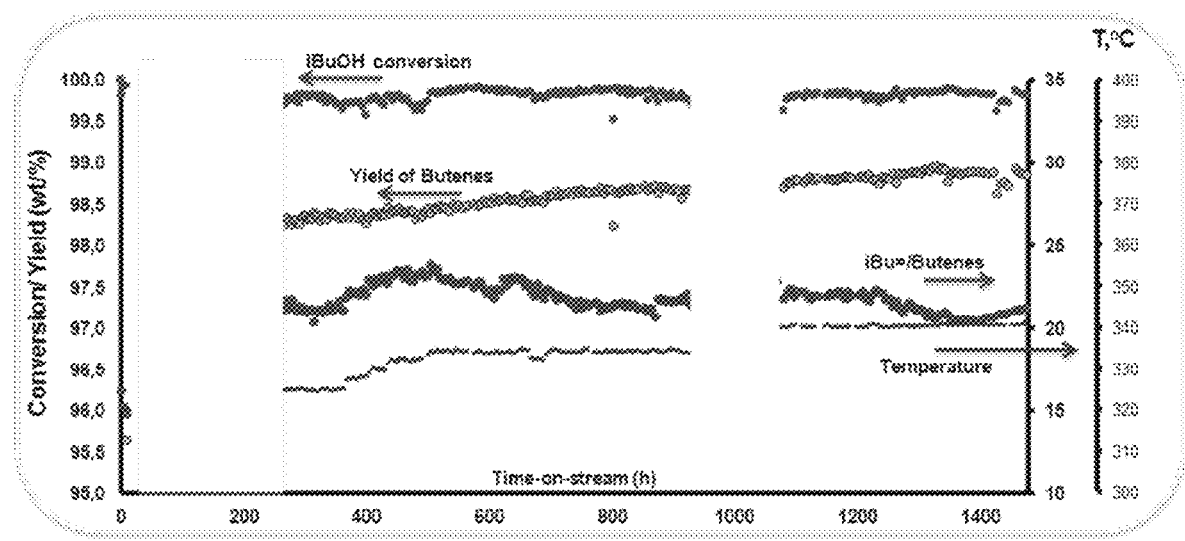
FIG. 2 illustrates for example 4 that the catalyst demonstrated a stable performance over more than 2000 hours.

The invention claimed is:

1. A process for the isomerizing dehydration of a feedstock comprising a primary monoalcohol, alone or as a mixture, of formula R—$CH_2$—OH, wherein R is a nonlinear alkyl radical of formula $C_nH_{2n+1}$ where n is 4, said process comprising
   providing the feedstock into a reactor in vaporized form, and
   performing isomerizing dehydration of said vaporized feedstock in a gas phase at a weighted average temperature of 275° C. to 400° C., at a pressure of 0.5 MPa to 0.9 MPa and at a WWH of 5 to 10 h$^{-1}$, and in the presence of a catalyst comprising at least one silicic binder that consists of amorphous silica, and at least one zeolite having at least one series of channels, the opening of which is defined by a ring of 8 oxygen atoms, which zeolite is ferrierite, wherein the content of zeolite in the catalyst is 50% to 90% by weight, and wherein the vaporized feedstock entering the reactor has a weight content of water of 6% to 35%.

2. The process as claimed in claim 1, wherein the at least one zeolite is ferrierite, which has an Si/Al molar ratio of 8 to 70.

3. The process as claimed in claim 1, wherein the catalyst consists of a ferrierite and a silicic binder.

4. The process as claimed in claim 1, wherein the content of water in the feedstock is 6% to 10%.

5. The process as claimed in claim 1, wherein the content of water in the feedstock is 10% to 15%.

6. The process as claimed in claim 1, wherein the temperature is 300° C. to 400° C. and the WWH is 7 h$^{-1}$ to 10 h$^{-1}$.

7. The process as claimed in claim 1, wherein the catalyst is not pre-coked.

8. The process as claimed in claim 1, wherein the at least one zeolite is ferrierite, which has an Si/Al molar ratio of 10 to 50.

9. The process as claimed in claim 1, wherein the content of zeolite in the catalyst is 60% to 80% by weight.

10. The process as claimed in claim 1, wherein the pressure is 0.8 to 0.9 MPa.

11. The process as claimed in claim 1, wherein the temperature is 400° C.

12. The process as claimed in claim 1, wherein the temperature is 350° C. to 400° C.

13. The process as claimed in claim 1, wherein the content of water in the feedstock is 6% to 7%.

14. The process as claimed in claim 1, wherein the initial butenes selectivity is greater than 94%.

15. The process as claimed in claim 1, wherein the content of water in the feedstock is 7%.

16. The process as claimed in claim 1, wherein the content of water in the feedstock is 6% to 15%.

17. The process as claimed in claim 1, wherein the content of water in the feedstock is 7% to 30%.

* * * * *